United States Patent
Yamaguchi

(10) Patent No.: US 9,606,437 B2
(45) Date of Patent: Mar. 28, 2017

(54) FLUORINE-CONTAINING COMPOUND, SUBSTRATE FOR PATTERN FORMATION, PHOTODEGRADABLE COUPLING AGENT, PATTERN FORMATION METHOD, AND COMPOUND

(71) Applicants: KANAGAWA UNIVERSITY, Yokohama (JP); NIKON CORPORATION, Tokyo (JP)

(72) Inventor: Kazuo Yamaguchi, Yokohama (JP)

(73) Assignees: KANAGAWA UNIVERSITY, Yokohama (JP); NIKON CORPORATION, Tokyo (JP)

( * ) Notice: Subject to any disclaimer, the term of this patent is extended or adjusted under 35 U.S.C. 154(b) by 0 days.

(21) Appl. No.: 14/635,583

(22) Filed: Mar. 2, 2015

(65) Prior Publication Data

US 2015/0168836 A1    Jun. 18, 2015

Related U.S. Application Data

(63) Continuation of application No. PCT/JP2013/073771, filed on Sep. 4, 2013.

(30) Foreign Application Priority Data

Sep. 4, 2012  (JP) ................. 2012-194531

(51) Int. Cl.
*G03F 7/004*    (2006.01)
*G03F 7/075*    (2006.01)
(Continued)

(52) U.S. Cl.
CPC .......... *G03F 7/0755* (2013.01); *C07C 49/825* (2013.01); *C07C 49/84* (2013.01);
(Continued)

(58) Field of Classification Search
CPC .......... G03F 7/055; G03F 7/20; G03F 7/2002; G03F 7/002; C07C 49/84; C07C 49/825;
(Continued)

(56) References Cited

U.S. PATENT DOCUMENTS 7,393,515 B2    7/2008   Hoshino et al.
7,829,501 B2    11/2010  Nakamura et al.
(Continued)

FOREIGN PATENT DOCUMENTS

EP    1 736 477 A1    12/2006
JP    2006-276643    10/2006
(Continued)

OTHER PUBLICATIONS

Chinese Office Action dated Jan. 26, 2016 in corresponding Chinese Patent Application No. 201380045709.7.
(Continued)

*Primary Examiner* — Amanda C Walke

(57) ABSTRACT

A fluorine-containing compound represented by a following general formula (1) is provided. [In the general formula (1), X represents a halogen atom or an alkoxy group, $R^1$ represents a branched chain or cyclic alkyl group having 3 to 10 carbon atoms, and $R^{f1}$ and $R^{f2}$ represent fluorinated alkoxy groups. n represents an integer of 0 or greater.]

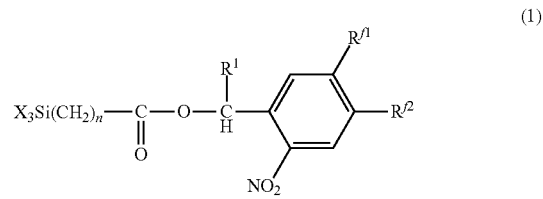

11 Claims, 2 Drawing Sheets

(51) Int. Cl.
  *H01L 21/027* (2006.01)
  *C07C 205/37* (2006.01)
  *C07C 205/45* (2006.01)
  *C07C 49/84* (2006.01)
  *C07F 7/18* (2006.01)
  *G03F 7/16* (2006.01)
  *C07C 49/825* (2006.01)
  *C07C 205/56* (2006.01)
  *G03F 7/20* (2006.01)
  *G03F 7/00* (2006.01)

(52) U.S. Cl.
  CPC .......... *C07C 205/37* (2013.01); *C07C 205/45* (2013.01); *C07C 205/56* (2013.01); *C07F 7/1836* (2013.01); *C07F 7/1852* (2013.01); *G03F 7/0046* (2013.01); *G03F 7/16* (2013.01); *G03F 7/20* (2013.01); *G03F 7/2002* (2013.01); *H01L 21/0274* (2013.01); *G03F 7/0002* (2013.01)

(58) Field of Classification Search
  CPC ... C07C 205/45; C07C 205/37; C07C 205/56; H01L 21/0274
  USPC .................. 430/322, 270.1, 271.1, 330, 331; 556/438; 560/221; 568/306, 337, 587
  See application file for complete search history.

(56) References Cited

U.S. PATENT DOCUMENTS

2006/0222865 A1 10/2006 Hoshino et al.
2008/0318779 A1 12/2008 Nakamura et al.

FOREIGN PATENT DOCUMENTS

| JP | 2007-23007 | 2/2007 |
| JP | 2008-50321 | 3/2008 |
| JP | 2008171978 A * | 7/2008 |
| WO | WO 2005/054256 A1 | 6/2005 |
| WO | WO 2006/016708 A1 | 2/2006 |

OTHER PUBLICATIONS

PCT International Search Report mailed Dec. 10, 2013 in corresponding International Patent Application No. PCT/JP2013/073771.
PCT Written Opinion of the International Searching Authority mailed Dec. 10, 2013 in corresponding International Patent Application No. PCT/JP2013/073771.
Zheng et al., "Design, Synthesis, and Structure—Activity Relationship, Molecular Modeling, and NMR Studies of a Series of Phenyl Alkyl Ketones as Highly Potent and Selective Phosphodiesterase-4 Inhibitors", Journal of Medicinal Chemistry, vol. 51, 2008, pp. 7673-7688.

* cited by examiner

FLUORINE-CONTAINING COMPOUND, SUBSTRATE FOR PATTERN FORMATION, PHOTODEGRADABLE COUPLING AGENT, PATTERN FORMATION METHOD, AND COMPOUND

CROSS-REFERENCE TO RELATED APPLICATION

Priority is claimed on Japanese Patent Application No. 2012-194531, filed on Sep. 4, 2012. This application is a continuation application of International Patent Application No. PCT/JP2013/073771, filed on Sep. 4, 2013. The contents of these applications are incorporated herein by reference.

BACKGROUND

Technical Field

The present invention relates to a fluorine-containing compound, a substrate for pattern formation, a photodegradable coupling agent, a pattern formation method, and a compound.

In recent years, in the manufacture of micro devices such as a semiconductor device, an integrated circuit, and a device for an organic EL display, a method in which a pattern having different surface characteristics is formed on a substrate, and a micro device is made by using the difference in the surface characteristics has been proposed.

As a pattern formation method using the difference in the surface characteristics of a substrate, there is a method in which a hydrophilic region and a water repellent region are formed on a substrate, and an aqueous solution of functional material is applied to the hydrophilic region.

In this method, the aqueous solution of functional material is wet and spread only in the hydrophilic region. Therefore, it is possible to form a thin film pattern of the functional material.

As the material capable of forming a hydrophilic region and a water repellent region on a substrate, in recent years, a coupling agent has been used. In Japanese Unexamined Patent Application, First Publication No. 2008-50321, a photodegradable coupling agent of which the contact angle before and after light irradiation can be significantly changed is described.

SUMMARY

However, in the photodegradable coupling agent as described in Japanese Unexamined Patent Application, First Publication No. 2008-50321, there is still room for improvement in a difference in the contact angles before and after light irradiation and sensitivity.

Aspects of the present invention are to provide a fluorine-containing compound useful as a coupling agent which has a large difference in contact angles before and after light irradiation and has more favorable sensitivity, a substrate for pattern formation using the fluorine-containing compound, a photodegradable coupling agent using the fluorine-containing compound, a pattern formation method, and a compound useful as an intermediate when preparing the fluorine-containing compound.

A first aspect of the present invention is a fluorine-containing compound represented by a following general formula (1).

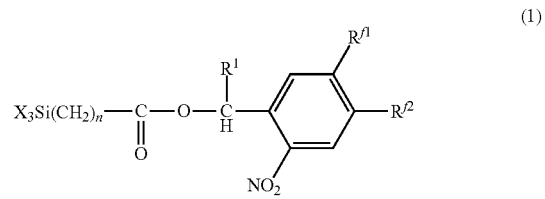

[In the general formula (1), X represents a halogen atom or an alkoxy group, $R^1$ represents a branched chain or cyclic alkyl group having 3 to 10 carbon atoms, and $R^{f1}$ and R are fluorinated alkoxy groups. n represents an integer of 0 or greater.]

A second aspect of the present invention is a substrate for pattern formation having a surface chemically modified with the fluorine-containing compound according to the first aspect.

A third aspect of the present invention is a photodegradable coupling agent formed of the fluorine-containing compound according to the first aspect.

A fourth aspect of the present invention is a pattern formation method for forming a pattern on a work surface of an object, which includes a first step of chemically modifying the work surface using the fluorine-containing compound according to the first aspect, a second step of generating a latent image formed of a hydrophilic region and a water repellent region by irradiating the chemically modified work surface with light having a predetermined pattern, and a third step of disposing a pattern formation material in the hydrophilic region or the water repellent region.

A fifth aspect of the present invention is a compound represented by a following general formula (f).

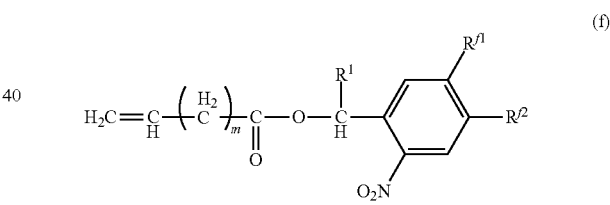

[In the general formula (f), $R^1$ represents a branched chain or cyclic alkyl group having 3 to 10 carbon atoms, $R^{f1}$ and $R_{f2}$ represent fluorinated alkoxy groups, and n represents an integer of 0 or greater.]

A sixth aspect of the present invention is a compound represented by a following general formula (e).

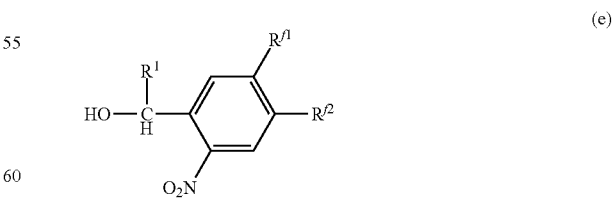

[In the general formula (e), $R^1$ represents a branched chain or cyclic alkyl group having 3 to 10 carbon atoms, and $R^{f1}$ and $R^{f2}$ are fluorinated alkoxy groups.]

A seventh aspect of the present invention is a compound represented by a following general formula (d).

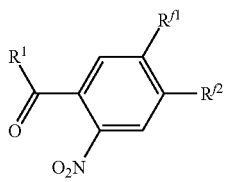

(d)

[In the general formula (d), $R^1$ represents a branched chain or cyclic alkyl group having 3 to 10 carbon atoms, and $R^{f1}$ and $R^{f2}$ are fluorinated alkoxy groups.]

An eighth aspect of the present invention is a compound represented by a following general formula (c).

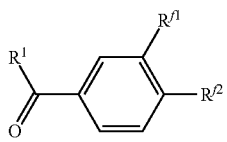

(c)

[In the general formula (c), $R^1$ represents a branched chain or cyclic alkyl group having 3 to 10 carbon atoms, and $R^{f1}$ and $R^{f2}$ are fluorinated alkoxy groups.]

According to the aspects of the present invention, a fluorine-containing compound useful as a coupling agent which has a large difference in contact angles before and after light irradiation and has more favorable sensitivity, a substrate for pattern formation using the fluorine-containing compound, a photodegradable coupling agent using the fluorine-containing compound, a pattern formation method, and a compound useful as an intermediate when preparing the fluorine-containing compound are provided.

DESCRIPTION OF EMBODIMENTS

<<Fluorine-Containing Compound>>

Figure 1:
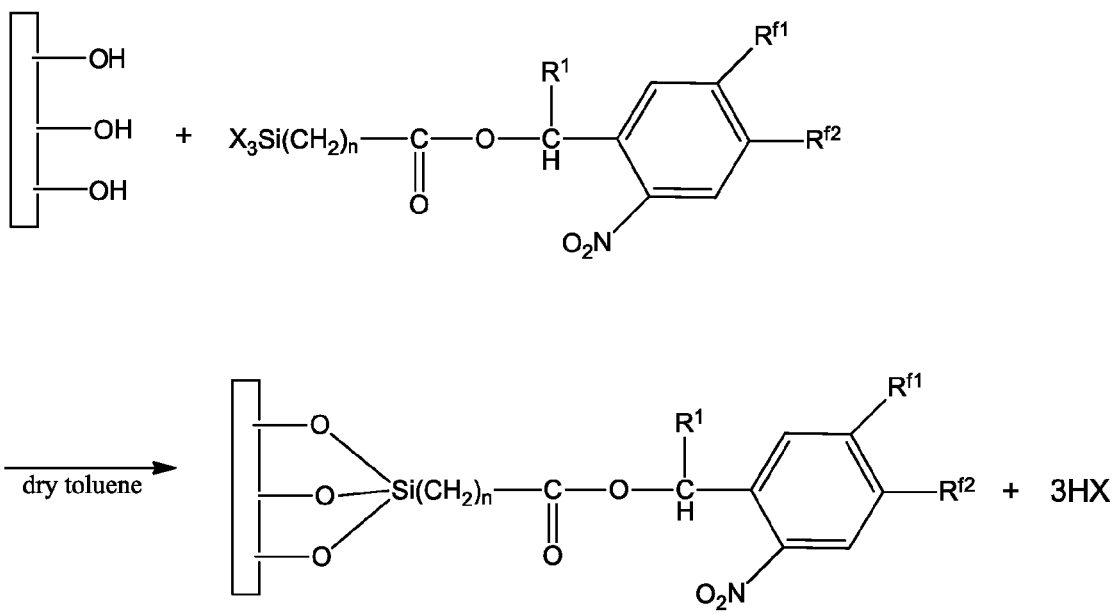
FIG. 1 is a schematic view showing a first step in a pattern formation method of the present invention.

A first aspect of the present invention is a fluorine-containing compound represented by the following general formula (1).

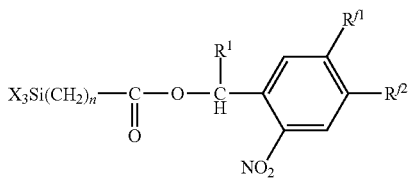

(1)

[In the general formula (1), X represents a halogen atom or an alkoxy group, $R^1$ represents a branched chain or cyclic alkyl group having 3 to 10 carbon atoms, and $R^{f1}$ and R are fluorinated alkoxy groups. n represents an integer of 0 or greater.]

In the formula (1), X represents a halogen atom or an alkoxy group. Examples of the halogen atom represented by X include a fluorine atom, a chlorine atom, a bromine atom, and an iodine atom. Here, X in the formula (1) is preferably an alkoxy group rather than a halogen atom. In the formula (1), n represents an integer. From the viewpoint of easy availability of starting materials, n is preferably an integer of 1 to 20, and more preferably an integer of 2 to 15.

In the general formula (1), $R^1$ represents a branched chain or cyclic alkyl group having 3 to 10 carbon atoms.

Examples of a branched chain alkyl group having 3 to 10 carbon atoms of $R^1$ in the formula (1) include such as an isobutyl group, an isopentyl group, a 2-methylbutyl group, a 2-methylpentyl group, a 3-methylpentyl group, a 4-methylpentyl group, a 2-ethylbutyl group, a 2-methylhexyl group, a 3-methylhexyl group, a 4-methylhexyl group, a 5-methylhexyl group, a 2-ethylpentyl group, a 3-ethylpentyl group, a 2-methylheptyl group, a 3-methylheptyl group, a 4-methylheptyl group, a 5-methylheptyl group, a 2-ethylhexyl group, a 3-ethylhexyl group, an isopropyl group, a sec-butyl group, a 1-ethylpropyl group, a 1-methylbutyl group, a 1,2-dimethylpropyl group, a 1-methylheptyl group, a 1-ethylbutyl group, a 1,3-dimethylbutyl group, a 1,2-dimethylbutyl group, a 1-ethyl-2-methylpropyl group, a 1-methylhexyl group, a 1-ethylheptyl group, a 1-propylbutyl group, a 1-isopropyl-2-methylpropyl group, a 1-ethyl-2-methylbutyl group, a 1-propyl-2-methylpropyl group, a 1-ethylhexyl group, a 1-propylpentyl group, a 1-isopropylpentyl group, a 1-isopropyl-2-methylbutyl group, a 1-isopropyl-3-methylbutyl group, a 1-methyloctyl group, a 1-propylhexyl group, a 1-isobutyl-3-methylbutyl group, a tert-butyl group, a tert-hexyl group, a tert-pentyl group, and a tert-octyl group.

In the formula (1), examples of a cyclic alkyl group having 3 to 10 carbon atoms of $R^1$ include such as a cyclopropyl group, a cyclobutyl group, a cyclopentyl group, a cyclohexyl group, a cycloheptyl group, a cyclooctyl group, and an adamantyl group.

In the formula (1), $R^1$ is preferably a group having 3 to 8 carbon atoms, more preferably a group having 3 to 6 carbon atoms, and particularly preferably a group having 3 to 5 carbon atoms.

In the formula (1), $R^1$ is preferably an isopropyl group, an isobutyl group, or a tert-butyl group, among the above-described branched chain or cyclic alkyl groups.

In the formula (1), $R^{f1}$ or $R^{f2}$ is a fluorinated alkoxy group. $R^{f1}$ or $R_{f2}$ is preferably a fluorinated alkoxy group having 5 or more carbon atoms. $R^{f1}$ or $R^{f2}$ may be the same as or different from each other, and are preferably the same.

Examples of the fluorinated alkoxy group of $R^{f1}$ or $R^{f2}$ include such as —O—$(CH_2)_3(CF_2)_3CF_3$, —O—$(CH_2)_3(CF_2)_4CF_3$, —O—$(CH_2)_4(CF_2)_4CF_3$, —O—$(CH_2)_4(CF_2)_5CF_3$, and —O—$(CH_2)_2(CF_2)_3CF_3$.

<<Compound>>

A fifth aspect of the present invention is a compound represented by the following general formula (f).

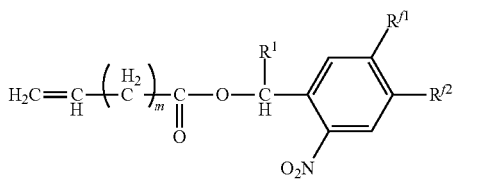

[In the general formula (f), $R^1$ represents a branched chain or cyclic alkyl group having 3 to 10 carbon atoms, $R^{f1}$ and Rf2 are fluorinated alkoxy groups, and m represents an integer of 0 or greater.]

In the above general formula (f), $R^1$, $R^{f1}$, and $R^{f2}$ are the same as $R^1$, $R^{f1}$, and $R^{f2}$ in the general formula (1). m in the above formula (f) represents an integer. From the viewpoint of easy availability of starting materials, m is preferably an integer of 1 to 20, and more preferably an integer of 2 to 15.

A sixth aspect of the present invention is a compound represented by the following general formula (e).

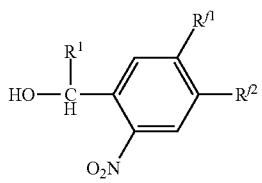

[In the general formula (e), $R^1$ represents a branched chain or cyclic alkyl group having 3 to 10 carbon atoms, and $R^{f1}$ and $R^{f2}$ are fluorinated alkoxy groups.]

In the above general formula (e), $R^1$, $R^{f1}$, and $R^{f2}$ are the same as $R^1$, $R^{f1}$, and $R^{f2}$ in the general formula (1).

A seventh aspect of the present invention is a compound represented by the following general formula (d).

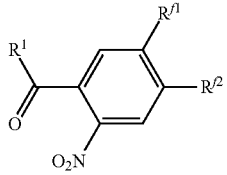

[In the general formula (d), $R^1$ represents a branched chain or cyclic alkyl group having 3 to 10 carbon atoms, and $R^{f1}$ and $R^{f2}$ are fluorinated alkoxy groups.]

In the above general formula (d), $R^1$, $R^{f1}$, and $R^{f2}$ are the same as $R^1$, $R^{f1}$, and $R^{f2}$ in the general formula (1).

An eighth aspect of the present invention is a compound represented by the following general formula (c).

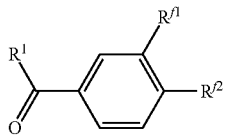

[In the general formula (c), $R^1$ represents a branched chain or cyclic alkyl group having 3 to 10 carbon atoms, and $R^{f1}$ and $R^{f2}$ are fluorinated alkoxy groups.]

In the above general formula (c), $R^1$, $R^{f1}$, and $R^{f2}$ are the same as $R^1$, $R^{f1}$, and $R^{f2}$ in the general formula (1).

The compounds according to the fifth to the eighth aspects of the present invention are useful as a raw material (intermediate) of the fluorine-containing compound according to the first aspect of the present invention.

<Preparation Method of Fluorine-Containing Compound>

The fluorine-containing compound of the present invention is preferably prepared using the compounds according to the fifth to the eighth aspects of the present invention as a raw material (intermediate).

Examples of the solvent used in the following steps include such as ethyl acetate, butyl acetate, acetone, methyl ethyl ketone, methyl isobutyl ketone, cyclohexanone, tetrahydrofuran, dioxane, N,N-dimethylformamide, N,N-dimethylacetamide, benzene, toluene, acetonitrile, methylene chloride, chloroform, dichloroethane, methanol, ethanol, 1-propanol, 2-propanol, and 1-butanol. These may be used alone or in combination of two or more kinds thereof.

[Step of Obtaining Compound According to Eighth Aspect]

The compound according to the eighth aspect of the present invention can be obtained by the following step.

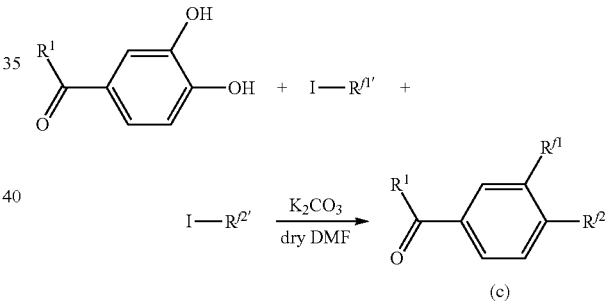

In the above reaction formula, $R^1$, $R^{f1}$, and $R^{f2}$ are the same as $R^1$, $R^{f1}$, and $R^{f2}$ in the general formula (1), —O—$R^{f1'}$ is $R^{f1}$, and —O—$R^{f2'}$ is $R^{f2}$.

[Step of Obtaining Compound According to Seventh Aspect]

The compound according to the seventh aspect of the present invention can be obtained by the following step.

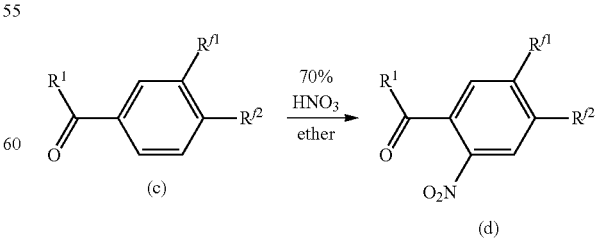

In the above reaction formula, $R^1$, $R^{f1}$, and $R^{f2}$ are the same as $R^1$, $R^{f1}$, and $R^{f2}$ in the general formula (1).

[Step of Obtaining Compound According to Sixth Aspect]

The compound according to the sixth aspect of the present invention can be obtained by the following step.

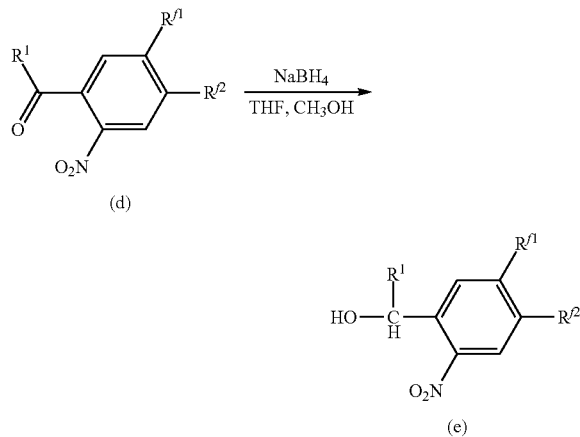

(d)

(e)

In the above reaction formula, $R^1$, $R^{f1}$, and $R^{f2}$ are the same as $R^1$, $R^{f1}$, and $R^{f2}$ in the general formula (1).

[Step of Obtaining Compound According to Fifth Aspect]

The compound according to the fifth aspect of the present invention can be obtained by the following step.

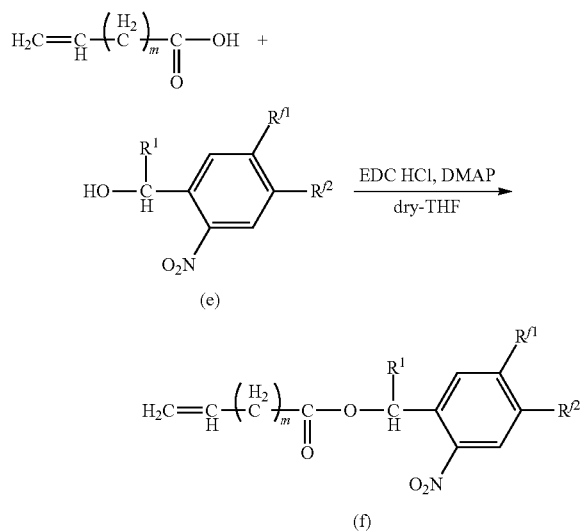

(e)

(f)

In the above reaction formula, $R^1$, $R^{f1}$, and $R^{f2}$ are the same as $R^1$, $R^{f1}$, and $R^{f2}$ in the general formula (1), and m is an integer of 0 or greater.

[Step of Obtaining Flourine-containing Compound According to First Aspect]

The fluorine-containing compound according to the first aspect of the present invention is obtained by a reaction of trimethoxysilane and the compound (f). In the following steps, a catalyst is preferably used, and a platinum-carbonylvinylmethyl complex (Ossko catalyst) or a platinum-divinyltetramethyldisiloxane complex (Karstedt catalyst) and the like can be used.

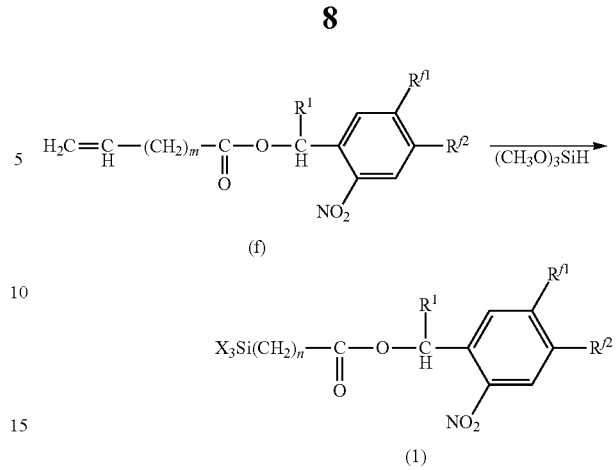

(f)

(1)

In the above reaction formula, $R^1$, $R^{f1}$, and $R^{f2}$ are the same as $R^1$, $R^{f1}$, and $R^{f2}$ in the general formula (1), and m and n are integers of 0 or greater.

In the above reaction formula, X, $R^1$, $R^{f1}$, $R^{f2}$, and n are the same as those in the general formula (1).

<<Substrate for Pattern Formation>>

A second aspect of the present invention is a substrate for pattern formation having a surface chemically modified with the fluorine-containing compound.

The substrate is not particularly limited, however, glass, quartz glass, a silicon wafer, a plastic plate, a metal plate, and the like are preferable. In addition, a substrate on which a metal thin film was formed may be used.

The shape of the substrate is not particularly limited, however, a plane surface, a curved surface, or a plane surface having partially a curved surface is preferable, and a plane surface is more preferable. In addition, the area of the substrate is also not particularly limited, however, a substrate having a large surface within a range in which applying methods in the related art can be applied can be employed. In addition, a surface chemically modified with the fluorine-containing compound is preferably formed on one side of the substrate on the plane surface.

When modifying the surface of a substrate, the substrate surface is preferably subjected to a pretreatment in advance. As the pretreatment method, a pretreatment in a piranha solution or a pretreatment by a UV-ozone cleaner is preferable.

The method for modifying the surface of a substrate is not particularly limited as long as it is a method in which X bonded to reactive Si, in the general formula (1), bonds to a substrate, however, known methods such as a dipping method and a chemical treatment method can be used.

<<Photodegradable Coupling Agent>>

A third aspect of the present invention is a photodegradable coupling agent formed of the fluorine-containing compound.

The photodegradable coupling agent of the aspects of the present invention has a photodegradable group with a liquid repellent group and an attaching group X linked to the photodegradable group through a functional group. The liquid repellent group has fluorinated alkoxy chains $R^{f1}$ and $R^{f2}$ at the terminal thereof. The functional group has a carboxy group as a residue after photodegradation. Therefore, in the photodegradable coupling agent of the present invention, a large difference in contact angles before and after light irradiation can be secured. That is, on the surface on which the photodegradable coupling agent was disposed, wettability (liquid repellency/hydrophilicity) significantly changes, and a comparatively large difference value between a contact angle (angle between the tangent line and the surface of a droplet) of the liquid (for example, water) on the surface before light irradiation and a contact angle of the liquid on the surface after light irradiation can be provided.

<<Pattern Formation Method>>

A fourth aspect of the present invention is a pattern formation method for forming a pattern on a work surface of an object, which includes a first step of chemically modifying the work surface using the fluorine-containing compound according to the first aspect, a second step of generating a latent image formed of a hydrophilic region and a water repellent region by irradiating the chemically modified work surface with light having a predetermined pattern, and a third step of disposing a pattern formation material in the hydrophilic region or the water repellent region.

[First Step]

The first step in the pattern formation method for forming a pattern on a work surface of an object is a step of chemically modifying the work surface using the fluorine-containing compound according to the first aspect.

The object is not particularly limited. In the present invention, examples thereof include a metal, a crystalline material (for example, single crystalline, polycrystal, and partially crystalline material), an amorphous material, a conductor, a semiconductor, an insulator, an optical element, a coated substrate, fiber, glass, ceramics, zeolite, plastic, a thermosetting and thermoplastic material (for example, doped in some cases: such as polyacrylate, polycarbonate, polyurethane, polystyrene, a cellulose polymer, polyolefin, polyamide, polyimide, a resin, polyester, polyphenylene), a film, a thin film, and a foil.

In the pattern formation method according to the aspects of the present invention, a circuit pattern for an electronic device is preferably formed on a substrate having flexibility.

In the present invention, as the substrate having flexibility which is an object, for example, a resin film or a foil of stainless steel or the like can be used. For example, as the resin film, materials such as a polyethylene resin, a polypropylene resin, a polyester resin, an ethylene vinyl copolymer resin, a polyvinyl chloride resin, a cellulose resin, a polyamide resin, a polyimide resin, a polycarbonate resin, a polystyrene resin, and a vinyl acetate resin can be used.

Here, the flexibility refers to properties capable of flexing the substrate without being broken or fractured even in a case where a force of about its own weight is added to the substrate. In addition, properties of bending by force of about its own weight are also included the flexibility. In addition, the flexibility varies depending on such as the material, the size, the thickness of the substrate, the environment such as temperature, or the like. Moreover, as the substrate, a single belt-shape substrate may be used, or the substrate may be configured to be formed in a belt-shape by connecting a plurality of unit substrates.

In the first step, the entire surface on a work surface of an object or a specific region is preferably chemically modified by using the fluorine-containing compound.

The method for chemically modifying a work surface of an object is not particularly limited as long as it is a method in which X bonded to reactive Si, in the general formula (1), bonds to a substrate, however, known methods such as a dipping method and a chemical treatment method can be used.

An example of the chemical modification in the first step is shown in FIG. 1.

[Second Step]

The second step is a step of generating a latent image formed of a hydrophilic region and a water repellent region by irradiating the chemically modified work surface with light having a predetermined pattern.

As the irradiation light, ultraviolet rays are preferable. The irradiation light preferably includes light having a wavelength included in a range of 200 nm to 450 nm, more preferably includes light having a wavelength included in a range of 320 nm to 450 nm. In addition, it is also preferable to be irradiated with light including light having a wavelength of 365 nm. Light having these wavelengths can efficiently degrade the photodegradable group according to the aspects of the present invention. Examples of a light source include a low-pressure mercury lamp, a high-pressure mercury lamp, an ultrahigh-pressure mercury lamp, a xenon lamp, a sodium lamp, a laser of a gas such as nitrogen, a liquid laser of organic dye solution, and a laser of a solid in which rare earth ions are contained in inorganic single crystals.

In addition, as a light source in which monochromatic light is obtained, other than the above lasers, light having a specific wavelength extracted from a broadband line spectrum or a continuous spectrum using an optical filter such as a band-pass filter or a cut-off filter may be used. The high-pressure mercury lamp or the ultrahigh-pressure mercury lamp is preferable as a light source since a large area can be irradiated with the mercury lamp at once.

In the pattern formation method of the present invention, a work surface can be irradiated with light arbitrarily in the above range. However, in particular, a work surface is preferably irradiated with light energy having a distribution corresponding to a circuit pattern.

In the second step, a residue (carboxy group) having hydrophilicity due to dissociation of a group having a water repellent performance by irradiating the chemically modified work surface with light having a predetermined pattern is produced. Therefore, after light irradiation, it is possible to generate a latent image formed of a hydrophilic region and a water repellent region.

In the second step, a latent image of a circuit pattern due to the difference in hydrophilicity and water repellency is preferably generated on the surface of a substrate having flexibility.

Figure 2:
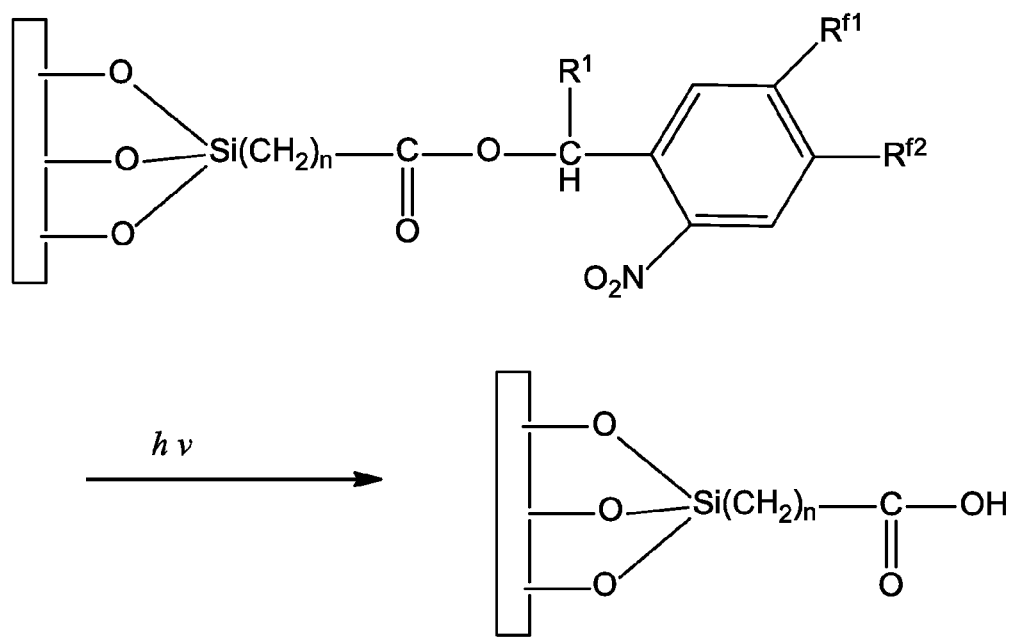
FIG. 2 is a schematic view showing a second step in the pattern formation method of the present invention.

FIG. 2 shows an example of a step in which a residue (carboxy group) having hydrophilicity due to dissociation of a group having a water repellent performance by irradiating the chemically modified work surface with light having a predetermined pattern is produced.

[Third Step]

A third step is a step of disposing a pattern formation material in a hydrophilic region or a water repellent region which is generated in the second step.

Examples of the pattern formation material include such as wiring materials (metal solution) in which particles of gold, silver, copper, or an alloy of these are dispersed in a predetermined solvent, electronic materials in which a precursor solution including the above-described metals, an insulator (resin), a semiconductor, an organic EL light-emitting material or the like is dispersed in a predetermined solvent, or a resist solution.

In the pattern formation method according to the aspects of the present invention, the pattern formation material is preferably a liquid conductive material, a liquid semiconductor material, or a liquid insulating material.

Examples of the liquid conductive material include a pattern formation material formed of a dispersion in which conductive fine particles are dispersed in a dispersion medium. As the conductive fine particles, for example, in addition to metal fine particles containing any of gold particles, silver particles, copper particles, palladium particles, nickel particles, and ITO particles, fine particles of oxides of the above metals, a conductive polymer, or superconductor can be used.

These conductive fine particles can also be used after the surfaces thereof are coated with an organic material in order to improve dispersibility.

The dispersion medium is not particularly limited as long as it can disperse the above-described conductive fine particles and does not aggregate. In addition to water, examples thereof include alcohols such as methanol, ethanol, propanol, and butanol, hydrocarbon-based compounds such as n-heptane, n-octane, decane, dodecane, tetradecane, toluene, xylene, cymene, durene, indene, dipentene, tetrahydronaphthalene, decahydronaphthalene, cyclohexyl benzene, ether-based compounds such as ethylene glycol dimethyl ether, ethylene glycol diethyl ether, ethylene glycol methyl ethyl ether, diethylene glycol dimethyl ether, diethylene glycol diethyl ether, diethylene glycol methyl ethyl ether, 1,2-dimethoxyethane, bis(2-methoxyethyl)ether, and p-dioxane, and polar compounds such as propylene carbonate, 7-butyrolactone, N-methyl-2-pyrrolidone, dimethyl formamide, dimethyl sulfoxide, and cyclohexanone. Among these, from the viewpoint of dispersibility of fine particles and stability of a dispersion and ease of application to a droplet discharge method (ink-jet method), water, alcohols, a hydrocarbon-based compound, and an ether-based compound are preferable, and as more preferable dispersion media, water and a hydrocarbon-based compound can be exemplified.

As the liquid semiconductor material, an organic semiconductor material dispersed or dissolved in a dispersion medium can be used. As the organic semiconductor material, a π-electron conjugated polymer material of which the skeleton is configured of conjugated double bonds is desired. Representative examples include soluble high-molecular materials such as polythiophene, poly(3-alkylthiophene), polythiophene derivatives, and pentacene.

As the liquid insulating material, an insulating material in which polyimide, polyamide, polyester, acryl, PSG (phosphorus glass), BPSG (boron phosphorus glass), polysilazane-based SOG, silicate-based SOG (Spin on Glass), alkoxy silicate-based SOG, or $SiO_2$ having a Si—$CH_3$ bond represented by a siloxane polymer, or the like is dispersed or dissolved in a dispersion medium can be exemplified.

In the third step, as a method for disposing a pattern formation material, a droplet discharge method, an ink-jet method, a spin-coating method, a roll-coating method, a slot-coating method, or the like can be applied.

Hereinafter, the pattern formation method according to the aspects of the present invention will be described with reference to a drawing.

Figure 3:
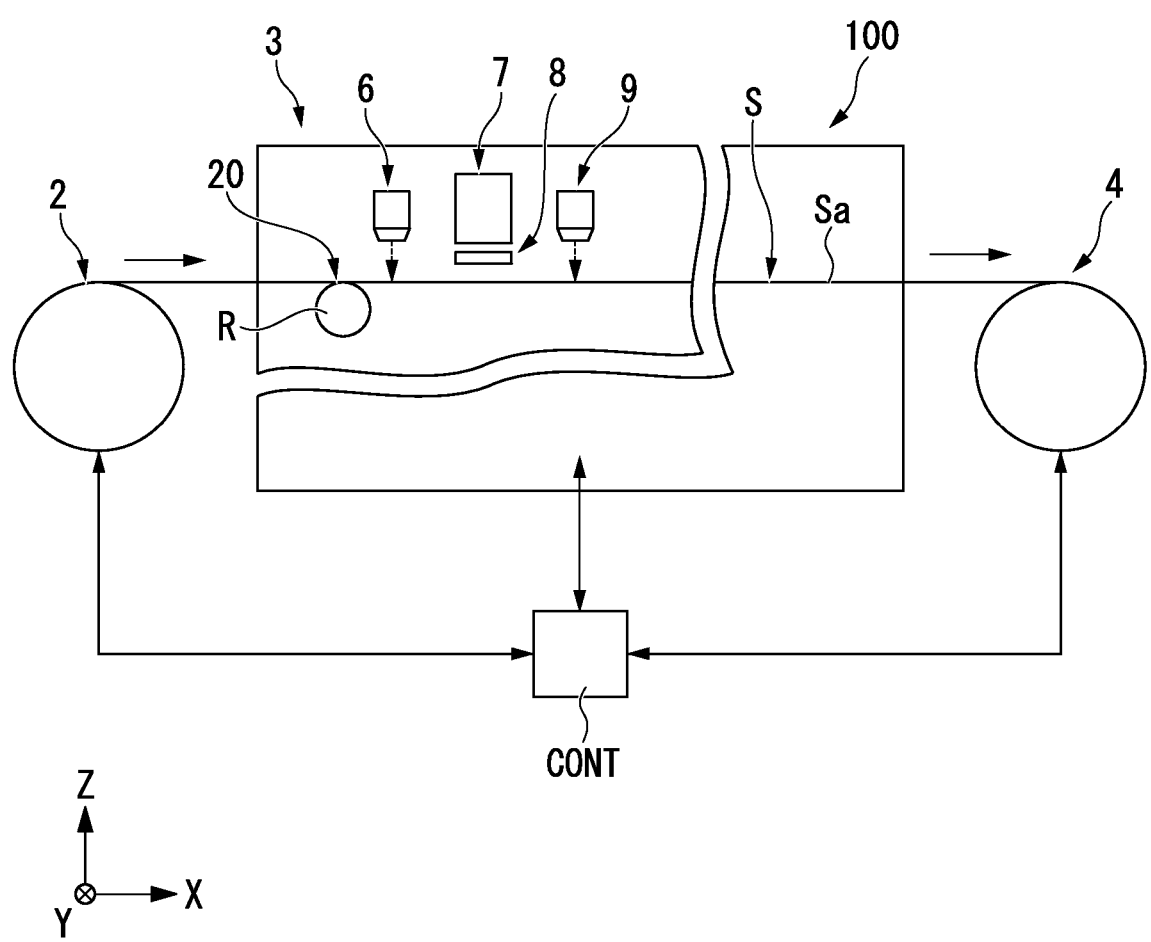
FIG. 3 is a schematic view showing an entire configuration of a preferable substrate processing apparatus in the pattern formation method of the present invention.

In the pattern formation method according to the aspects of the present invention, in a case where a substrate having flexibility corresponding to a so-called roll-to-roll process is used, a pattern may be formed by using a substrate processing apparatus 100 which is a roll-to-roll apparatus, as shown in FIG. 3. FIG. 3 shows a configuration of the substrate processing apparatus 100.

As shown in FIG. 3, the substrate processing apparatus 100 has a substrate supplying part 2 that supplies a belt-shape substrate (for example, a belt-shape film member) S, a substrate processing part 3 that performs a treatment with respect to the surface (work surface) Sa of the substrate S, a substrate-retrieving part 4 that retrieves the substrate S, an applying part 6 of a fluorine-containing compound, an exposing part 7, a mask 8, a patterning material-applying part 9, and a controller CONT that controls each of these parts. In the substrate processing part 3, various treatments can be performed on the surface of the substrate S between from the time when the substrate S is sent from the substrate supplying part 2 to the time when the substrate S is retrieved by the substrate-retrieving part 4.

The substrate processing apparatus 100 can be suitably used in a case where a display element (electronic device) such as an organic EL element or a liquid crystal display element is formed on the substrate S.

Moreover, FIG. 3 is an illustration of a method using a photomask to generate a desired pattern light. However, the aspects of the present invention can also be suitably applied to a maskless exposure method in which a photomask is not used. As the maskless exposure method in which a desired pattern light is generated without using a photomask, a method in which a spatial light modulation element such as a DMD is used and a method in which a spot light is scanned as a laser beam printer can be exemplified.

In the pattern formation method according to the aspects of the present invention, a XYZ coordinate system is set as shown in FIG. 3. Hereinafter, description is made using the XYZ coordinate system as appropriate. In the XYZ coordinate system, for example, an X-axis and a Y-axis are set along a horizontal plane, and a Z-axis is set upward along the vertical direction. In addition, the substrate processing apparatus 100 transports the substrate S from the minus side (−X-axis side) to the plus side (+X-axis side), along the X-axis as a whole. At this time, the width direction (short direction) of the belt-shape substrate S is set in the Y-axis direction.

As the substrate S which is a work surface in the substrate processing apparatus 100, for example, a resin film or a foil of stainless steel or the like can be used. For example, as the resin film, materials such as a polyethylene resin, a polypropylene resin, a polyester resin, an ethylene vinyl copolymer resin, a polyvinyl chloride resin, a cellulose resin, a polyamide resin, a polyimide resin, a polycarbonate resin, a polystyrene resin, and a vinyl acetate resin can be used.

For example, the substrate S preferably has a small thermal expansion coefficient such that the size is not changed even in a case of receiving heat of about 200° C. For example, the thermal expansion coefficient can be reduced by mixing inorganic filler with a resin film. Examples of the inorganic filler include such as titanium oxide, zinc oxide, alumina, and silicon oxide. In addition, the substrate S may be a single body of ultrathin glass having a thickness of about 100 um manufactured by a float method or the like or a laminate formed by adhering the resin film or aluminum foil on the ultrathin glass.

The size of the width direction (short direction) of the substrate S, for example, is formed to be about 1 m to 2 m, and the size of the length direction (long direction), for example, is formed to be 10 m or greater. Needless to say, the sizes are only examples, and are not limited thereto. For example, the size of the Y-axis direction of the substrate S may also be 50 cm or less, or may also be 2 m or greater. In addition, the size of the X-axis direction of the substrate S may also be 10 m or less.

The substrate S is preferably formed so as to have flexibility. Here, the flexibility refers to properties capable of flexing the substrate without being broken or fractured even in a case where a force of about its own weight is added to the substrate. In addition, properties of bending by a force of about its own weight are also included in the flexibility.

In addition, the flexibility varies depending on such as the material, the size, the thickness of the substrate, the environment such as temperature, or the like. Moreover, as the substrate S, a single belt-shape substrate may be used, or the substrate S may be configured to be formed in a belt-shape by connecting a plurality of unit substrates.

The substrate supplying part 2, for example, supplies the substrate S wound in a roll shape by sending the substrate S to the substrate processing part 3. In this case, in the substrate supplying part 2, a rotation driving device or the like that rotates a shaft portion winding the substrate S or the shaft portion is provided. In addition, the substrate supplying part 2 may have a configuration in which a cover portion that covers the substrate S in the state of being wound in a roll shape or the like is provided. Moreover, the substrate supplying part 2 is not limited to the mechanism for sending the substrate S wound in a roll shape, and may include a mechanism (for example, a nip type driving roller or the like) for sequentially sending the belt-shape substrate S in the length direction.

The substrate-retrieving part 4 retrieves the substrate S passed through the substrate processing apparatus 100, for example, by winding in a roll shape. In the substrate-retrieving part 4, the same as in the substrate supplying part 2, a rotation driving source that rotates a shaft portion for winding the substrate S or the shaft portion, a cover portion that covers the retrieved substrate S, or the like is provided. Moreover, in a case where the substrate S is cut into a panel shape or the like in the substrate processing part 3, for example, the substrate processing part 3 may have a configuration in which the substrate S is retrieved in a different state from the state of being wound in a roll shape, as a configuration in which the substrate S is retrieved in a stacked state.

The substrate processing part 3 transports the substrate S supplied from the substrate supplying part 2 to the substrate-retrieving part 4, and performs a step of chemically modifying the work surface Sa of the substrate S in a process of transporting using a fluorine-containing compound, a step of irradiating a chemically modified work surface with light having a predetermined pattern, and a step of disposing a pattern formation material. The substrate processing part 3 has the fluorine-containing compound-applying part 6 that applies a fluorine-containing compound to the work surface Sa of the substrate S, the exposing part 7 that irradiates with light, the mask 8, the patterning material-applying part 9, and a transporting device 20 that includes a driving roller R or the like to send the substrate S under the conditions corresponding to the form of processing.

As the fluorine-containing compound-applying part 6 or the patterning material-applying part 9, droplet application devices (for example, a droplet discharge type application device, an ink-jet type application device, a spin-coating type application device, a roll-coating type application device, and a slot-coating type application device) can be exemplified.

Each of these devices is suitably provided along the transport path of the substrate S, and is configured to be able to produce a flexible display panel or the like by a so-called roll-to-roll method. In the present embodiment, the exposing part 7 is provided, and devices performing the steps before and after thereof (photosensitive layer-forming step, photosensitive layer-developing step, or the like) are also provided in an in-line type, if necessary.

Since the fluorine-containing compound according to the aspects of the present invention has a photodegradable group with a water repellent group having a fluorinated alkoxy chain at the terminal, in a case where the fluorine-containing compound is attached on the substrate surface, the contact angle between the surface thereof and a liquid can be increased. In addition, a residue (carboxy group) having hydrophilicity can be produced by dissociating a group having a water repellent performance by irradiating with light. Therefore, before and after light irradiation, the substrate surface exhibits excellent hydrophilicity, and the contact angle can be reduced.

In addition, it is considered that in a case where a branched chain alkyl group having 3 to 5 carbons is present near the photodegradable group, a group having a water repellent performance can be dissociated with less energy (exposure amount).

EXAMPLES

Hereinafter, the present invention will be specifically described by the examples, and the present invention is not limited to the following examples.

[Synthesis of Fluorine-containing Compound (1)]

9.02 g (65.4 mmol) of 1,2-dimethoxybenzene, 0.311 g (2.45 mmol) of iodine crystals, and 20.7 g (131 mmol) of isobutyric acid anhydride were put into a 100 mL recovery flask, the recovery flask was refluxed at 170° C. for 6 hours, and after the temperature in the recovery flask was returned to room temperature, stirring was performed for 31 hours. Thereafter, 80 mL of H$_2$O was added to the recovery flask, and the organic layer was extracted with diethyl ether (80 mL×3). The extracted organic layer was washed with 5% NaHCO$_3$ (80 mL), a saturated saline solution (80 mL), and H$_2$O (80 mL), dried over anhydrous MgSO$_4$, filtered, and concentrated. Thereafter, the organic layer subjected to the above treatment was isolated and purified by column chromatography (hexane:ethyl acetate=4:1), and concentration and vacuum drying were performed, thereby obtaining a compound (a) (1-(3,4-dimethoxyphenyl)-2-methyl-1-propanone) as a pale yellow viscous matter.

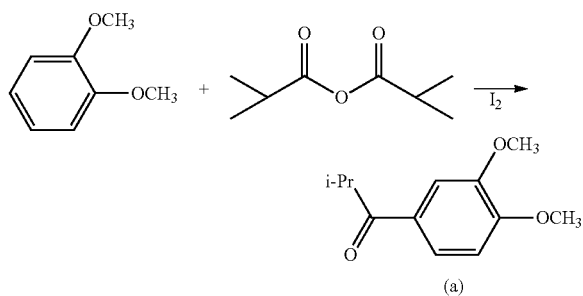

Identification results of the above-synthesized compound (a) are shown below.

Yield 3.90 g (18.7 mmol, 29%)

$R_f$ 0.27 (hexane:ethyl acetate = 4:1)

$^1H$-NMR (CDCl$_3$/TMS) 400 MHz $\delta$ = 1.22 (6H, d, J = 6.8 Hz)(CH$_3$)$_2$
= 3.55 (1H, sep, J = 6.8 Hz)(CH$_3$)$_2$
= 3.94 and 3.95 (6H, s, s) Ar-OCH$_3$ × 2
= 6.90 (1H, d, J = 8.4 Hz) Ar-H
= 7.55 (1H, d, J = 2.0 Hz) Ar-H
= 7.60 (1H, d, d, J = 8.4 Hz) Ar-H IR (NaCl)

1674 cm$^{-1}$ (C=O)

Next, 2.73 g (13.1 mmol) of the compound (a) was put into a 100 mL two-neck recovery flask, and 50 mL of dry-N,N-dimethylformamide (hereinafter, referred to as dry-DMF) and 11.2 g (262 mmol: 20 eq) of LiCl were added thereto in a nitrogen atmosphere. The two-neck recovery flask was refluxed at 170° C. for 29 hours, and the inside of the two-neck recovery flask was stirred at 100° C. for 32 hours. Thereafter, 200 mL of a saturated saline solution and 50 mL of 2 N HCl were added to the two-neck recovery flask, and the organic layer was extracted with ethyl acetate (150 mL×3). The extracted organic layer was dried over anhydrous MgSO$_4$, filtered, concentrated, and vacuum-dried. Thereafter, the organic layer subjected to the above treatment was isolated and purified by column chromatography (hexane:ethyl acetate=2:1), and concentration and vacuum drying were performed, thereby obtaining a compound (b) (1-(3,4-dihydroxyphenyl)-2-methyl-1-propanone) as a yellow viscous matter.

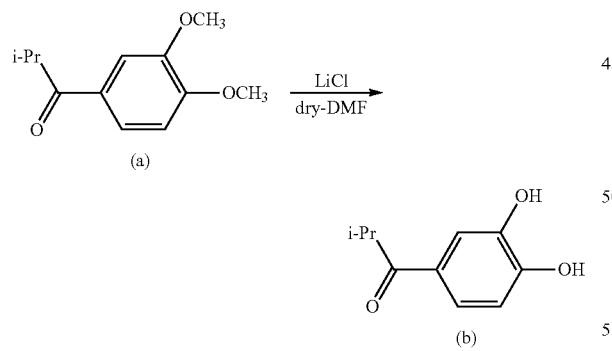

Identification results of the above-synthesized compound (b) are shown below.

Yield 1.50 g (hexane:ethyl acetate = 2:1)

$R_f$ 0.20 (hexane:ethyl acetate = 2:1)

$^1H$-NMR (CDCl$_3$/TMS) 400 MHz $\delta$ = 1.21 (6H, d, J = 6.8 Hz)(CH$_3$)$_2$
= 3.53 (1H, sep, J = 6.9 Hz) – CH
= 6.35 (1H, s) Ar-OH
= 6.94 (1H, d, J = 8.4 Hz) Ar-H
= 7.39 (1H, s) Ar-OH
= 7.52 (1H, d, d, J = 8.4 Hz) Ar-H
= 7.83 (1H, d, J = 2.0 Hz) Ar-H IR (NaCl)

3349 cm$^{-1}$ (OH)

1656 cm$^{-1}$ (C=O)

1.02 g (5.67 mmol) of the compound (b), 15 mL of dry DMF, and 1.57 g (11.3 mmol: 2 eq) of K$_2$CO$_3$ were put into a 100 mL two-neck recovery flask, and the resultant product was stirred at room temperature for 2 hours. Thereafter, 7 mL of dry DMF was added to 4.64 g (12.0 mmol: 2.1 eq) of 1-iodine-1H,1H,2H,2H,3H,3H-perfluoroheptane, then, this was added dropwise to the two-neck recovery flask, and the inside of the two-neck recovery flask was stirred at 60° C. for 14 hours. After the reaction solution was distilled off under reduced pressure, 60 mL of H$_2$O and 20 mL of 2 N HCl were added thereto, and the organic layer was extracted with ethyl acetate (60 mL×4). The extracted organic layer was washed with a saturated saline solution (60 mL×5). The organic layer was dried over anhydrous MgSO$_4$, filtered, concentrated, and vacuum-dried, thereby obtaining a compound (c) (1-(3,4-di(1H,1H,2H,2H,3H,3H-perfluoroheptyloxy)phenyl)-2-methyl-1-propanone) as an orange solid.

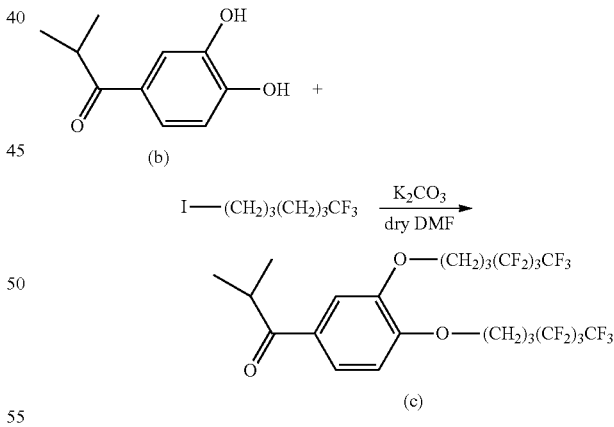

Identification results of the above-synthesized compound (c) are shown below.

Yield 3.62 g (5.17 mmol, 91%)

$R_f$ 0.73 (hexane:ethyl acetate = 2:1)

$^1H$-NMR (CDCl$_3$/TMS) 400 MHz

δ = 1.21 (6H, d, J = 6.8 Hz)(CH$_3$)$_2$
= 2.15 to 2.19 (4H, m) -O-CH$_2$-CH$_2$-CH$_2$-CF$_2$- ×2
= 2.32 to 2.34 (4H, m) -O-CH$_2$-CH$_2$-CH$_2$-CF$_2$- ×2
= 3.53 (1H, sep, J = 6.9 Hz) -CH-
= 4.13 and 4.14 (4H, t, t) -O-CH$_2$-CH$_2$-CH$_2$-CF$_2$- ×2
= 6.88 (1H, d, J = 8.5 Hz) Ar-H
= 7.52 (1H, d, J = 2.0 Hz) Ar-H
= 7.58 (1H, dd, J = 8.4 Hz) Ar-H IR (KBr)
722 cm$^{-1}$ (CF$_3$)
1226 cm$^{-1}$ (CF$_2$, CF$_3$)
1678 cm$^{-1}$ (C=O)

0.502 g (0.717 mmol) of the compound (c) was put into a 100 mL recovery flask, and the compound (c) was dissolved in 3 mL of diethyl ether. 5 mL of 70% NHO$_3$ was added little by little to the recovery flask provided in an ice bath, and the inside of the recovery flask provided in the ice bath was stirred for 1.5 hours. Next, the reaction solution was poured into ice, then, the organic layer was extracted with 50 mL of H$_2$O and ethyl acetate (50 mL×3), and the extracted organic layer was washed with 5% NaHCO$_3$ (50 mL×3). The organic layer was dried over anhydrous MgSO$_4$, filtered, and concentrated. Recrystallization of the compound was performed by dissolving the concentrated product in 20 mL of ethanol. Suction filtration and vacuum drying of the crystals were performed, thereby obtaining a compound (d) 1-(2-nitro-4,5-di(1H,1H,2H,2H,3H,3H-perfluoroheptyloxy)phenyl)-2-methyl-1-propanone) as a light yellow needle-like crystal.

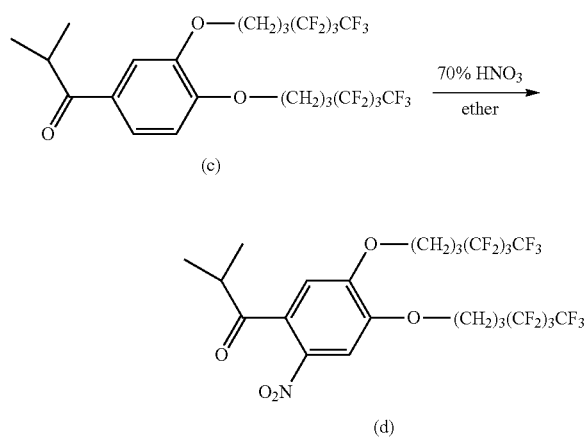

Identification results of the above-synthesized compound (d) are shown below.

Yield 0.256 g (3.43 mmol, 48%)
$R_f$ 0.40 (hexane:ethyl acetate = 6:1)
$^1$H-NMR (CDCl$_3$/TMS) 400 MHz
δ = 1.21 (6H, d, J = 6.8 Hz) (CH$_3$)$_2$ = 2.15 to 2.23 (4H, m) —O—CH$_2$—CH$_2$—CH$_2$—CF$_2$— x 2
= 2.27 to 2.34 (4H, m) —O—CH$_2$—CH$_2$—CH$_2$—CF$_2$— x 2
= 2.89 (1H, sep) —CH—
= 4.16 and 4.17 (4H, t, t) —O—CH$_2$—CH$_2$—CH$_2$—CF$_2$— x 2
= 6.67 (1H, s) Ar—H
= 7.64 (1H, s) Ar—H IR (KBr)
721 cm$^{-1}$ (CF$_3$)
1228 cm$^{-1}$ (CF$_2$, CF$_3$)
1358 and 1523 cm$^{-1}$ (NO$_2$)
1703 cm$^{-1}$ (C=O)

2.96 g (3.97 mmol) of the compound (d), 12 mL of tetrahydrofuran (hereinafter, referred to as THF), and 8 mL of methanol were put into a 100 mL recovery flask, then, 0.300 g (7.94 mmol: 2eq) of NaBH$_4$ was added little by little to the recovery flask provided in an ice bath, and the inside of the recovery flask was stirred for 90 minutes. Thereafter, the inside of the recovery flask was stirred at room temperature for 30 minutes. The reaction solution was concentrated, and the organic layer was extracted with 60 mL of H$_2$O, 20 mL of 2 N HCl, and ethyl acetate (50 mL×3). The extracted organic layer was dried over anhydrous MgSO$_4$, filtered, and concentrated. The organic layer subjected to the above treatment was isolated and purified by column chromatography (hexane:ethyl acetate=6:1), and concentration and vacuum drying were performed, thereby obtaining a compound (e) (1-(2-nitro-4,5-di(1H,1H,2H,2H,3H,3H-perfluoroheptyloxy)phenyl)-2-methyl-1-propanol) as a yellow viscous matter.

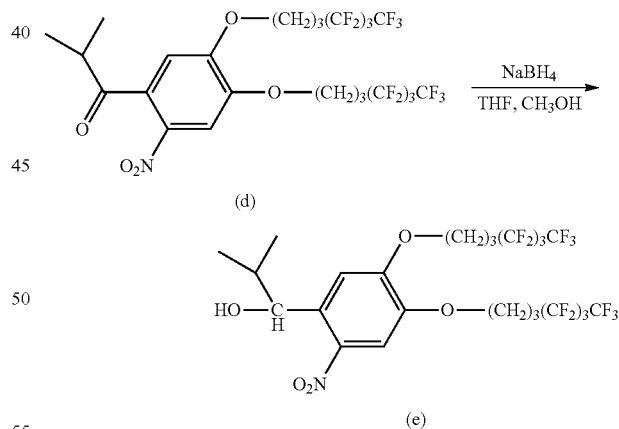

Identification results of the above-synthesized compound (e) are shown below.

Yield 2.17 g (2.90 mmol, 76%)
$R_f$ 0.20 (hexane:ethyl acetate = 6:1)
$^1$H-NMR (CDCl$_3$/TMS) 400 MHz δ = 0.94 and 0.96 (6H, d, J = 6.8 Hz)(CH₃)₂
= 1.97 to 2.03 (1H, m) -CH-
= 2.14 to 2.21 (5H, m) -O-CH₂-CH₂-CH₂-CF₂- ×2
  Ar-CH-OH
= 2.27 to 2.40 (4H, m) -O-CH₂-CH₂-CH₂-CF₂- ×2
= 4.08 to 4.23 (4H, m) -O-CH₂-CH₂-CH₂-CF₂- ×2
= 5.27 (1H, d, J = 8.5 Hz) Ar-H
= 7.20 (1H, s) Ar-H
= 7.55 (1H, s) Ar-H IR (KBr)

742 cm⁻¹ (CF₃)

1228 cm⁻¹ (CF₂, CF₃)

1334 and 1522 cm⁻¹ (NO₂)

3547 cm⁻¹ (OH)

0.803 g (mmol: 1.5 eq) of carbodiimide hydrochloride and 10 mL of THF were put into a 100 mL two-neck recovery flask in a nitrogen atmosphere, and the resultant product was stirred for 10 minutes in the two-neck recovery flask provided in an ice bath. Thereafter, 2.09 g (2.79 mmol: 1 eq) of the compound (e), 0.567 g (5.58 mmol: 2 eq) of 4-pentenoic acid, and 0.412 g (3.35 mmol: 1.2 eq) of N,N-dimethyl-4-aminopyridine (hereinafter, referred to as DMAP) were dissolved in 10 mL of dry-THF, and the resultant product was added dropwise to the two-neck recovery flask. After the inside of the two-neck recovery flask was stirred for 10 minutes, the two-neck recovery flask was taken out from the ice bath, and the inside of the two-neck recovery flask was stirred at room temperature for 14 hours. The reaction solution was concentrated, and 40 mL of H₂O and 10 mL of 2 N HCl were added thereto. The organic layer was extracted with ethyl acetate (50 mL×3), and the extracted organic layer was washed with 5% NaHCO₃ (50 mL×3). The organic layer was dried over anhydrous MgSO₄, filtered, and concentrated. The organic layer subjected to the above treatment was isolated and purified by column chromatography (hexane:ethyl acetate=6:1), and concentration and vacuum drying were performed, thereby obtaining a compound (f) (1-(2-nitro-4,5-di(1H,1H,2H,2H,3H,3H-perfluoroheptyloxy)phenyl-2-methylpropyl 4-pentenoic acid ester) as a pale yellow solid.

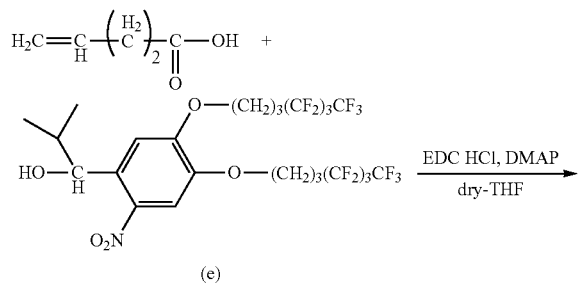

(e)

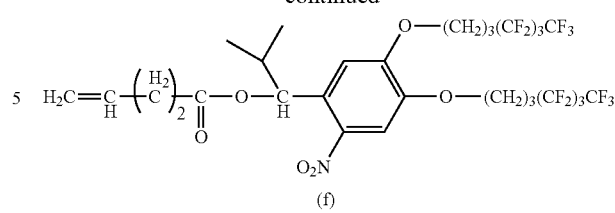

(f)

Identification results of the above-synthesized compound (f) are shown below.

Yield 2.13 g (2.57 mmol, 92%)

$R_f$ 0.40 (hexane:ethyl acetate = 8:1)

¹H-NMR (CDCl₃/TMS) 400 MHz

δ = 0.98 and 1.00 (6H, d, J = 6.8 Hz) (CH₃)₂
= 2.13 to 2.21 (5H, m) -O-CH₂-CH₂-CH₂-CF₂- ×2
  -CH-(CH₃)₂
= 2.26 to 2.52 (8H, m) -O-CH₂-CH₂-CH₂-CF₂- ×2
  -CH₂-CH₂-COO-
= 4.10 to 4.15 (4H, m) -O-CH₂-CH₂-CH₂-CF₂- ×2
= 4.98 to 5.06 (2H, m) CH₂=CH-
= 5.74 to 5.84 (1H, m) CH₂=CH-
= 6.31 (1H, d, J = 5.8 Hz) Ar-CH-CH-(CH₃)₂
= 6.87 (1H, s) Ar-H
= 7.57 (1H, s) Ar-H IR (KBr)

720 cm⁻¹ (CF₃)

122 cm⁻¹ (CF₂, CF₃)

1332 and 1525 cm⁻¹ (NO₂)

1732 cm⁻¹ (C = O)

1.01 g (1.22 mmol) of the compound (f) was put into a 50 mL two-neck recovery flask, and vacuum drying was performed for 1.5 hours. Thereafter, 1 mL of dry-THF, 1.49 g (12.2 mmol: 10 eq) of trimethoxysilane, 7 drops of a Karstedt catalyst were added to the two-neck recovery flask, and the inside of the two-neck recovery flask was stirred at room temperature for 2.5 hours. The reaction solution was concentrated, the obtained organic layer was isolated by medium pressure column chromatography (hexane:ethyl acetate:tetramethoxysilane=8:1:0.09), and concentration and vacuum drying were performed, thereby obtaining a fluorine-containing compound (1) (1-(2-nitro-4,5-di(1H,1H,2H,2H,3H,3H-perfluoroheptyloxy)phenyl))-2-methylpropyl 5-(trimethoxysilyl)pentenoic acid ester) as a pale yellow solid.

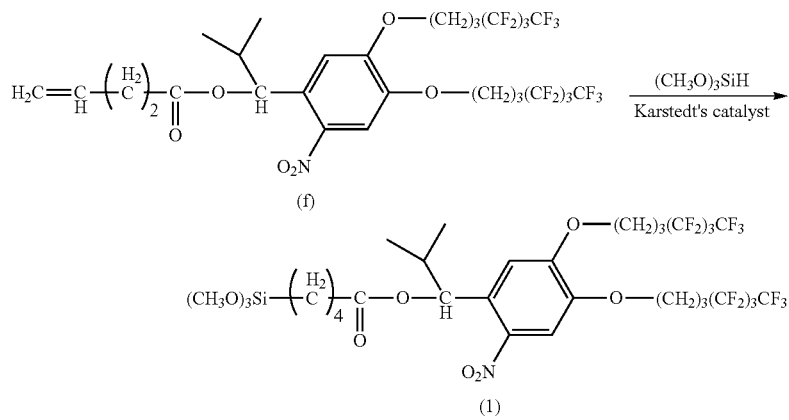

Identification results of the above-synthesized fluorine-containing compound (1) are shown below.

Yield 0.775 g (0.814 mmol, 67%)

$R_f$ 0.23 (hexane:ethyl acetate = 8:1)

$^1H$-$NMR$ (CDCl$_3$/TMS) 400 MHz $\delta$ = 0.61 to 0.67 (2H, m) -CH$_2$-

= 0.97 and 0.99 (6H, d, J = 6.8 Hz) -(CH$_3$)$_2$

= 1.39 to 1.47 (2H, m) -Si-CH$_2$-CH$_2$-

= 1.66 (2H, quint, J = 7.6 Hz) -CH$_2$-CH$_2$-COO-

= 2.12 to 2.21 (5H, m) -O-CH$_2$-CH$_2$-CH$_2$-CF$_2$- ×2

-CH-(CH$_3$)$_2$

= 2.26 to 2.39 (6H, m) -O-CH$_2$-CH$_2$-CH$_2$-CF$_2$- ×2

-CH$_2$-COO-

= 3.55 (9H, s) (CH$_3$O)$_3$-Si-

= 4.08 to 4.17 (4H, m) -O-CH$_2$-CH$_2$-CH$_2$-CF$_2$- ×2

= 6.30 (1H, d, J = 5.8 Hz) Ar-CH-CH-(CH$_3$)$_2$

= 6.87 (1H, s) Ar-H

= 7.57 (1H, s) Ar-H

IR (KBr)

7.20 cm$^{-1}$ (CF$_3$)

1227 cm$^{-1}$ (CF$_2$, CF$_3$)

1332 and 1525 cm$^{-1}$ (NO$_2$)

1729 cm$^{-1}$ (C=O)

[Synthesis of Fluorine-Containing Compound (2)]

10.1 g (72.4 mmol) of 1,2-dimethoxybenzene, 0.553 g (4.36 mmol) of iodine crystals, and 20.4 g (109 mmol) of pivalic acid anhydride were put into a 100 mL recovery flask, and the inside of the recovery flask was refluxed at 170° C. for 9 hours, and at 100° C. for 17 hours. Thereafter, H$_2$O (80 mL) was added to the recovery flask, and the organic layer was extracted with diethyl ether (80 mL×3). The extracted organic layer was washed with a 5% aqueous sodium hydrogen carbonate solution (80 mL), a saturated saline solution (80 mL×2), and H$_2$O (80 mL×3), dried over anhydrous MgSO$_4$, filtered, and concentrated. The organic layer subjected to the above treatment was isolated and purified by column chromatography (hexane:ethyl acetate=4:1), and concentration and vacuum drying were performed, thereby obtaining a compound (a1) (1-(3,4-dimethoxyphenyl)-2,2-dimethyl-1-propanone) as a pale yellow viscous matter.

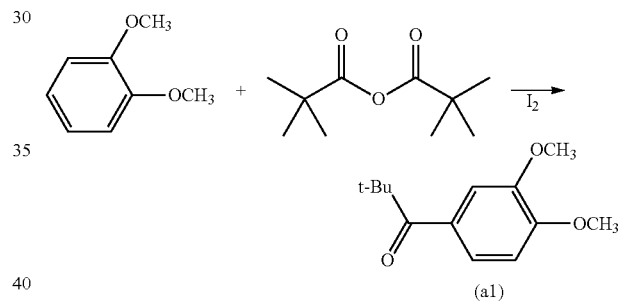

Identification results of the above-synthesized compound (a1) are shown below.

Yield 3.89 g (17.4 mmol, 24%)

$R_f$ 0.33 (hexane:ethyl acetate = 4:1)

$^1H$-$NMR$ (CDCl$_3$/TMS) 400 MHz $\delta$ = 1.39 (9H, s) (CH$_3$)$_3$

= 3.92 and 3.93 (6H, s, s) Ar-OCH$_3$ ×2

= 6.90 (1H, d, J = 8.4 Hz) Ar-H

= 7.55 (1H, d, J = 2.0 Hz) Ar-H

= 7.60 (1H, d, J = 8.4 Hz) Ar-H

IR (NaCl)

1663 cm$^{-1}$ (C=O)

3.01 g (13.5 mmol) of the compound (a1) was put into a 100 mL two-neck recovery flask, and 35 mL of dry-DMF and 11.5 g (271 mmol: 20 eq) of LiCl were added to the two-neck recovery flask in a nitrogen atmosphere. The inside of the two-neck recovery flask was refluxed at 170° C.

for 46 hours. Thereafter, 150 mL of a saturated saline solution, 100 mL of $H_2O$, and 50 mL of 2 N HCl were added to the two-neck recovery flask, then, the organic layer was extracted with ethyl acetate (100 mL×3), and the extracted organic layer was dried over anhydrous $MgSO_4$, filtered, and concentrated. Thereafter, the organic layer subjected to the above treatment was isolated and purified by column chromatography (hexane:ethyl acetate=6:1), and concentration and vacuum drying were performed, thereby obtaining a compound (b1) (1-(3,4-dihydroxyphenyl)-2,2-dimethyl-1-propanone) as a brown solid.

then, 60 mL of $H_2O$ and 20 mL of 2 N HCl were added to the two-neck recovery flask, and the organic layer was extracted with ethyl acetate (60 mL×3). The extracted organic layer was washed with a saturated saline solution (60 mL×5). The organic layer was dried over anhydrous $MgSO_4$, filtered, concentrated, and vacuum-dried, thereby obtaining a compound (c1) (1-(3,4-di(1H,1H,2H,2H,3H,3H-perfluoroheptyloxy)phenyl)-2,2-dimethyl-1-propanone) as an orange solid.

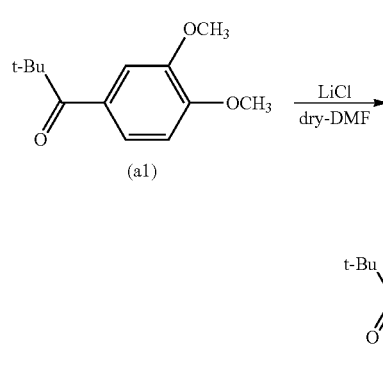

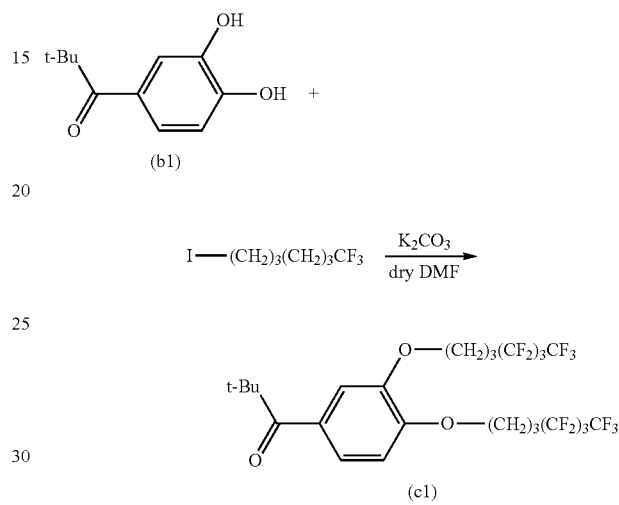

Identification results of the above-synthesized compound (b1) are shown below.

Yield 2.12 g (10.9 mmol, 81%)

$R_f$ 0.33 (hexane:ethyl acetate = 2:1)

$^1H$-$NMR$ ($CDCl_3$/$TMS$) 400 MHz $\delta$ = 1.39 (9$H$, $s$) ($CH_3$)$_3$

= 6.27 (1$H$, $s$) Ar-OH

= 6.88 (1$H$, $d$, $J$ = 8.4 Hz) Ar-H

= 7.25 (1$H$, $s$) Ar-OH

= 7.47 (1$H$, $d$, $J$ = 8.4 Hz) Ar-H

= 7.68 (1$H$, $d$, $J$ = 2.1 Hz) Ar-H

IR(KBr)

3321 $cm^{-1}$ (OH)

1642 $cm^{-1}$ (C=O)

1.75 g (9.00 mmol) of the compound (b1), 20 mL of dry DMF, and 2.50 g (18.0 mmol: 2 eq) of $K_2CO_3$ were put into a 100 mL two-neck recovery flask, and the inside of the two-neck recovery flask was stirred at room temperature for 2 hours. Thereafter, 10 mL of dry DMF was added to 7.39 g (18.9 mmol: 2.1 eq) of 1-iodine-1H,1H,2H,2H,3H,3H-perfluoroheptane, then, this was added dropwise to the two-neck recovery flask, and the inside of the two-neck recovery flask was stirred at 60° C. for 21 hours. The reaction solution was distilled off under reduced pressure, Identification results of the above-synthesized compound (c1) are shown below.

Yield 4.99 g (6.98 mmol, 78%)

$R_f$ 0.78 (hexane:ethyl acetate = 2:1)

$^1H$-$NMR$ ($CDCl_3$/$TMS$) 400 MHz $\delta$ = 1.38 (9$H$, $s$) ($CH_3$)$_3$

= 2.10 to 2.19 (4$H$, $m$) -O-$CH_2$-$CH_2$-$CH_2$-$CF_2$- ×2

= 2.27 to 2.40 (4$H$, $m$) -O-$CH_2$-$CH_2$-$CH_2$-$CF_2$- ×2

= 4.10 and 4.12 (4$H$, $t$, $t$) -O-$CH_2$-$CH_2$-$CH_2$-$CF_2$- ×2

= 6.83 (1$H$, $d$, $J$ = 8.6 Hz) Ar-H

= 7.40 (1$H$, $d$, $J$ = 2.0 Hz) Ar-H

= 7.53 (1$H$, $d$, $J$ = 8.5 Hz) Ar-H

IR (KRr)

721 $cm^{-1}$ ($CF_3$)

1228 $cm^{-1}$ ($CF_2$, $CF_3$)

1669 $cm^{-1}$ (C=O)

4.55 g (6.37 mmol) of the compound (c1) was put into a 300 mL recovery flask, and the compound (c1) was dissolved in 25 mL of diethyl ether. 40 mL of 70% $HNO_3$ was added little by little to the recovery flask provided in an ice bath, and the inside of the recovery flask provided in the ice bath was stirred for 20 minutes. Thereafter, ice water was added to the reaction solution, then, the organic layer was extracted with 80 mL of H₂O and ethyl acetate (60 mL×3), and the extracted organic layer was washed with an aqueous saturated sodium hydrogen carbonate solution (60 mL×6). The organic layer was dried over anhydrous MgSO₄, filtered, and concentrated, thereby obtaining a yellow solid (d1) including a by-product. 3.00 g (3.94 mmol) of the yellow solid (d1), 12 mL of THF, and 8 mL of methanol were put into a 100 mL recovery flask, then, 0.307 g (8.12 mmol: 2eq) of NaBH₄ was added little by little to the recovery flask provided in an ice bath, and the inside of the recovery flask was stirred for 30 minutes. Thereafter, the inside of the recovery flask was stirred at room temperature for 1 hour. The reaction solution was concentrated, then, the organic layer was extracted with 50 mL of H₂O, 20 mL of 2 N HCl, and ethyl acetate (60 mL×3), and the extracted organic layer was washed with a saturated saline solution (50 mL×1) and H₂O (50 mL×1). The organic layer was dried over anhydrous MgSO₄, filtered, and concentrated. The organic layer subjected to the above treatment was isolated and purified by column chromatography (hexane:ethyl acetate=9:1), and concentration and vacuum drying were performed, thereby obtaining a compound (e1) (1-(2-nitro-4,5-di(1H,1H,2H,2H,3H,3H-perfluoroheptyloxy)phenyl)-2,2-dimethyl-1-propanol) as a yellow viscous matter.

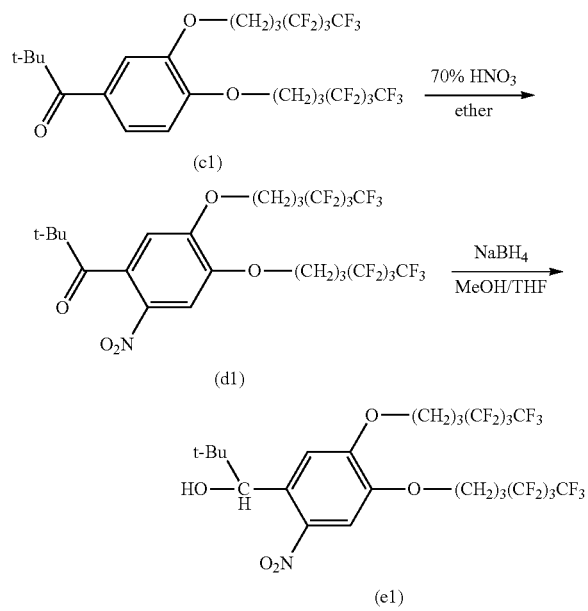

Identification results of the above-synthesized compound (e1) are shown below.

Yield 1.72 g (2.25 mmol, 35%)

$R_f$ 0.17 (hexane:ethyl acetate = 6:1)

$^1H$-NMR (CDCl₃/TMS) 400 MHz $\delta = 0.892$ (9H, s) -C-(CH₃)₃

= 2.03 (1H, d, J = 3.9 Hz) Ar-CH-OH

= 2.17 to 2.20 (4H, m) -O-CH₂-CH₂-CH₂-CF₂- ×2

= 2.27 to 2.39 (4H, m) -O-CH₂-CH₂-CH₂-CF₂- ×2

= 4.09 to 4.22 (4H, m) -O-CH₂-CH₂-CH₂-CF₂- ×2

= 5.61 (1H, d, J = 3.8 Hz) Ar-CH-C-(CH₃)₃

= 7.22 (1H, s) Ar-H

= 7.43 (1H, s) Ar-H sIR(NaCl)

721 cm⁻¹ (CF₃)

1228 cm⁻¹ (CF₂, CF₃)

1335 and 1516 cm⁻¹ (NO₂)

3456 cm⁻¹ (OH)

0.472 g (2.46 mmol: 1.5 eq) of EDC.HCl and 5 mL of THF were put into a 100 mL two-neck recovery flask in a nitrogen atmosphere, and the inside of the two-neck recovery flask provided in an ice bath was stirred for 10 minutes. Thereafter, 1.20 g (1.58 mmol: 1 eq) of the compound (e1), 0.327 g (3.27 mmol: 2 eq) of 4-pentenoic acid, and 0.251 g (2.05 mmol: 1.2 eq) of DMAP were dissolved in 5 mL of dry-THF, and the resultant product was added dropwise to the two-neck recovery flask. After the inside of the two-neck recovery flask was stirred for 10 minutes, the two-neck recovery flask was taken out from the ice bath, and the inside of the two-neck recovery flask was stirred at room temperature for 21 hours. The reaction solution was concentrated, then, 40 mL of H₂O and 10 mL of 2 N HCl were added to the two-neck recovery flask, and the organic layer was extracted with ethyl acetate (50 mL×3). The extracted organic layer was washed with an aqueous saturated sodium hydrogen carbonate solution (50 mL×3). The organic layer was dried over anhydrous MgSO₄, filtered, and concentrated. The organic layer subjected to the above treatment was isolated and purified by column chromatography (hexane:ethyl acetate=9:1), and concentration and vacuum drying were performed, thereby obtaining a compound (f1) (1-(2-nitro-4,5-di(1H,1H,2H,2H,3H,3H-perfluoroheptyloxy)phenyl)-2,2-dimethylpropyl 4-pentenoic acid ester) as a pale yellow solid.

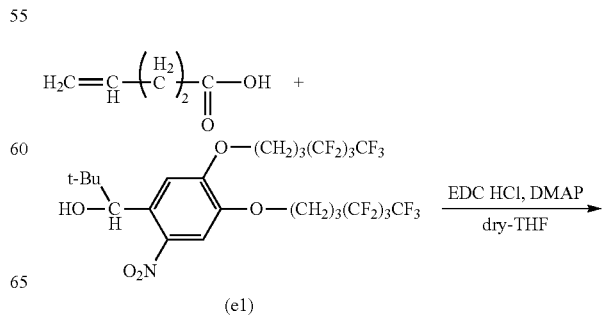

-continued

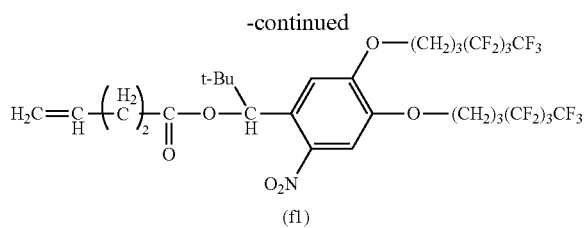

Identification results of the above-synthesized compound (f1) are shown below.

to the two-neck recovery flask in a nitrogen atmosphere, and the inside of the two-neck recovery flask was stirred at room temperature for 2.5 hours. The reaction solution was concentrated, the obtained organic layer was isolated by medium pressure column chromatography (hexane:ethyl acetate:tetramethoxysilane=8:1:0.09), and concentration and vacuum drying were performed, thereby obtaining a fluorine-containing compound (2) (1-(2-nitro-4,5-di(1H,1H,2H,2H,3H,3H-perfluoroheptyloxy)phenyl)-2,2-dimethyl-propyl 5-(trimethoxysilyl)pentenoic acid ester) as a pale yellow solid.

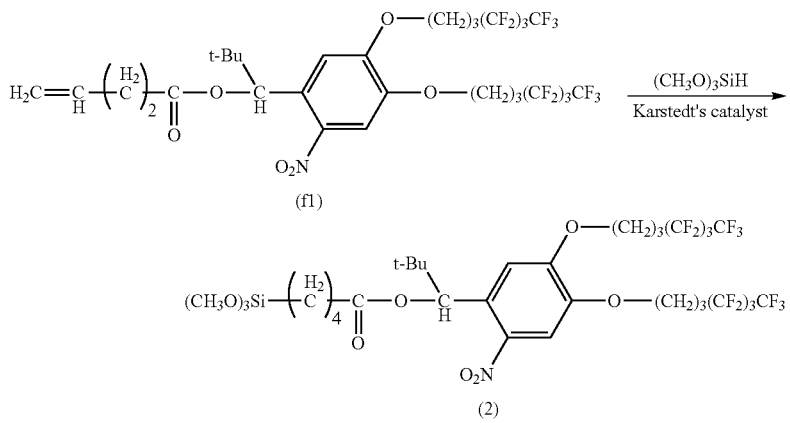

Yield 1.23 g (1.45 mmol, 92%)

$R_f$ 0.60 (hexane:ethyl acetate = 6:1)

$^1H$-NMR (CDCl$_3$/TMS) 400 MHz $\delta$ = 0.958 (9H, s) (CH$_3$)$_3$

= 2.13 to 2.21 (4H, m) -O-CH$_2$-CH$_2$-CH$_2$-CF$_2$- ×2

= 2.26 to 2.54 (8H, m) -O-CH$_2$-CH$_2$-CH$_2$-CF$_2$- ×2

-CH$_2$-CH$_2$-COO-

= 4.10 to 4.15 (4H, m) -O-CH$_2$-CH$_2$-CH$_2$-CF$_2$- ×2

= 4.98 to 5.07 (2H, m) CH$_2$=CH-

= 5.75 to 5.85 (1H, m) CH$_2$=CH-

= 6.64 (1H, s) Ar-CH-C-(CH$_3$)$_3$

= 6.89 (1H, s) Ar-H

= 7.54 (1H, s) Ar-H

IR (KBr)

720 cm$^{-1}$ (CF$_3$)

1225 cm$^{-1}$ (CF$_2$, CF$_3$)

1339 and 1526 cm$^{-1}$ (NO$_2$)

1732 cm$^{-1}$ (C=O)

0.986 g (1.02 mmol) of the compound (f1) was put into a 50 mL two-neck recovery flask, and the inside of the two-neck recovery flask was vacuum-dried for 1 hour. Thereafter, dry-THF, 1.25 g (10.2 mmol: 10 eq) of trimethoxysilane, 7 drops of a Karstedt catalyst were added Identification results of the above-synthesized compound (2) are shown below.

Yield 0.775 g (0.814 mmol, 67%)

$R_f$ 0.20 (hexane:ethyl acetate:tetramethoxysilane= 8:1:0.09)

$^1H$-NMR (CDCl$_3$/TMS) 400 MHz $\delta$ = 0.620 to 0.661 (2H, m) -Si-CH$_2$-

= 0.959 (9H, s) (CH$_3$)$_3$

= 1.42 to 1.49 (2H, m) -Si-CH$_2$-CH$_2$-

= 1.68 (2H, quint, J = 7.6 Hz) -CH$_2$-CH$_2$-COO-

= 2.14 to 2.21 (4H, m) -O-CH$_2$-CH$_2$-CH$_2$-CF$_2$- ×2

= 2.23 to 2.41 (6H, m) -O-CH$_2$-CH$_2$-CH$_2$-CF$_2$- ×2

-CH$_2$-COO-

= 3.55 (9H, s) (CH$_3$O)-Si-

= 4.10 to 4.13 (4H, m) -O-CH$_2$-CH$_2$-CH$_2$-CF$_2$- ×2

= 6.63 (1H, s) Ar-CH-C-(CH$_3$)$_3$

= 6.90 (1H, s) Ar-H

= 7.54 (1H, s) Ar-H

IR (KBr)

720 cm$^{-1}$ (CF$_3$)

1228 cm$^{-1}$ (CF$_2$, CF$_3$)

1338 and 1528 cm$^{-1}$ (NO$_2$)

1729 cm$^{-1}$ (C=O)

<<Pretreatment>>

Four sheets of silicon wafer (3 cm×1.5 cm), two sheets of silicon wafer (2 cm×1 cm), and one sheet of quartz glass (4 cm×1 cm) were subjected to a pretreatment with a piranha solution or a UV-ozone cleaner, respectively.

Pretreatment in Piranha Solution

A mixed solution of $H_2SO_4:H_2O_2=7:3$ (14 mL:6 mL) was adjusted in a 50 mL recovery flask, then, two sheets of the silicon wafer (2 cm×1 cm) back to back were put thereinto, and the inside of the recovery flask was heated to 100° C. for one hour in an oil bath. Thereafter, the two sheets of the silicon wafer was washed with pure water, pure water was put into the recovery flask, ultrasonic cleaning was performed for 10 minutes, and the silicon wafers were dried in a stream of nitrogen.

Pretreatment in UV-Ozone Cleaner

Silicon wafer and quartz glass were subjected to ultrasonic cleaning for 5 minutes with methanol, water, and acetone, respectively. The substrate was taken out, dried in a stream of nitrogen, and pretreated with a UV-ozone cleaner. Oxygen injection into the UV-ozone cleaner was performed at a flow rate of 6 L/min for 3 minutes, and UV irradiation was performed for 1.5 hours. The generated ozone was discharged by flowing nitrogen at a flow rate of 6 L/min for 10 minutes. For quartz glass, in order to uniformly treat both sides of the substrate, washing was performed twice by the UV-ozone while turning the substrate.

<<Surface Modification with Fluorine-Containing Compound (1)>>

40 mL of dry toluene and 38.1 mg (40.0 μmol) of the fluorine-containing compound (1) were put into a 50 mL recovery flask, thereby preparing a 1 mM solution in the recovery flask. From the 1 mM solution, 20 mL of the solution was transferred to another 50 mL recovery flask. The pretreated silicon wafer and quartz glass were put into two recovery flasks separately, and the silicon wafer and the quartz glass were refluxed for 3 hours in nitrogen, respectively. The substrate was taken out from the recovery flask, and washed with methanol. Methanol and the substrate were put into in a sample bottle, and ultrasonic cleaning was performed (10 minutes). Furthermore, the substrate was washed with chloroform, then, chloroform and the substrate were put into in a sample bottle, and ultrasonic cleaning was performed (10 minutes). The surface of the substrate was dried with nitrogen, and a contact angle thereof was measured. After the measurement of contact angle, the surface of the substrate was dried with nitrogen, and the substrate was put into a sample bottle. The sample bottle was filled with nitrogen, and the substrate was stored. The following Table 1 shows the contact angles of the substrates after the surface modification.

Here, in the following Table 1, No. 7 and No. 8 show the results of the surface (No. 7) and the rear surface (No. 8) of one sheet of substrate.

TABLE 1

| No. | Type of substrate | Pretreatment | Contact angle (°) | Standard deviation |
| --- | --- | --- | --- | --- |
| 1 | Silicon wafer | Piranha solution | 93.8 | 1.5 |
| 2 | Silicon wafer | Piranha solution | 94.2 | 1.1 |
| 3 | Silicon wafer | UV-ozone | 96.1 | 0.7 |
| 4 | Silicon wafer | UV-ozone | 97.6 | 1.2 |
| 5 | Silicon wafer | UV-ozone | 97.5 | 0.9 |
| 6 | Silicon wafer | UV-ozone | 96.2 | 0.2 |

TABLE 1-continued

| No. | Type of substrate | Pretreatment | Contact angle (°) | Standard deviation |
| --- | --- | --- | --- | --- |
| 7 | Quartz glass | UV-ozone | 94.8 | 0.2 |
| 8 | Quartz glass | UV-ozone | 95.3 | 0.2 |

As shown in Table 1, regardless of the types of substrate or pretreatment methods, contact angles after the surface modification became values with the same degree as 94° to 98°.

<<Surface Modification with Fluorine-Containing Compound (2)>>

40 mL of dry toluene and 38.6 mg (40.0 μmol) of the fluorine-containing compound (2) were put into a 50 mL recovery flask, thereby preparing a 1 mM solution in the recovery flask. From the 1 mM solution, 20 mL of the solution was transferred to another 50 mL recovery flask. The pretreated silicon wafer and quartz glass were put into two recovery flasks separately, and the silicon wafer and the quartz glass were dipped for 3 hours in a nitrogen atmosphere, respectively. The substrate was taken out from the inside of the recovery flask, and washed with methanol. Methanol and the substrate were put into in a sample bottle, and ultrasonic cleaning was performed (10 minutes). Furthermore, the substrate was washed with chloroform, then, chloroform and the substrate were put into in a sample bottle, and ultrasonic cleaning was performed (10 minutes). The surface of the substrate was dried with nitrogen, and a contact angle thereof was measured. The following Table 2 shows the contact angles of the substrates after the surface modification.

Here, in the following Table 2, No. 9 and No. 10 show the results of the surface (No. 9) and the rear surface (No. 10) of one sheet of substrate.

TABLE 2

| No. | Type of substrate | Pretreatment | Contact angle (°) | Standard deviation |
| --- | --- | --- | --- | --- |
| 1 | Silicon wafer | UV-ozone | 99.7 | 0.5 |
| 2 | Silicon wafer | UV-ozone | 99.4 | 0.7 |
| 3 | Silicon wafer | UV-ozone | 99.2 | 1.2 |
| 4 | Silicon wafer | UV-ozone | 100.2 | 0.7 |
| 5 | Silicon wafer | UV-ozone | 99.8 | 0.6 |
| 6 | Silicon wafer | UV-ozone | 100.0 | 0.7 |
| 7 | Silicon wafer | UV-ozone | 99.6 | 0.3 |
| 8 | Silicon wafer | UV-ozone | 100.4 | 0.9 |
| 9 | Quartz glass | UV-ozone | 101.1 | 1.4 |
| 10 | Quartz glass | UV-ozone | 98.9 | 0.7 |

As shown in Table 2, contact angles of all substrates after the surface modification became values near 100°.

<<Light Irradiation onto Modified Substrate>>

The position of 50 mW/cm$^2$ was detected using a luminometer, then, the pretreatment was performed on that position by the UV-ozone, and a surface modified substrate was placed. Light having a wavelength of 320 nm or greater was applied thereto using an ultrahigh-pressure mercury lamp.

The modified substrate after the light irradiation was washed with methanol, and washed with chloroform in the same manner. The modified substrate and chloroform were put into a sample bottle, and ultrasonic cleaning was performed (10 minutes). The modified substrate was taken out using tweezers, then, the surface of the modified substrate was dried in a stream of nitrogen, and a contact angle thereof was measured. The results are shown in Table 3.

TABLE 3

| | Compound | Contact angle before exposure/ after exposure | Exposure amount (J/cm$^2$) |
|---|---|---|---|
| Example 1 | 1 | 98/51 | 18 |
| Example 2 | 2 | 100/51 | 18 |
| Comparative Example 1 | 3 | 69/55 | 12 |
| Comparative Example 2 | 4 | 73/50 | 7.5 |
| Comparative Example 3 | 5 | 97/57 | 30 |

In Table 3, the compounds 1 and 2 are the fluorine-containing compounds (1) and (2), and the compounds 3 to 5 are the following compounds (13) to (15).

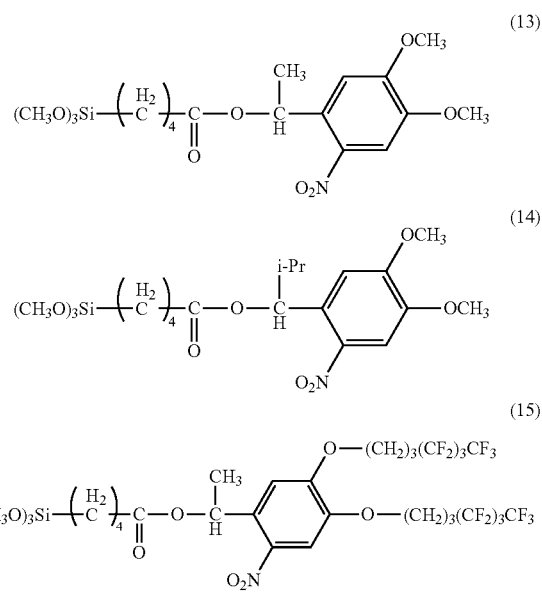

As shown in the above results, Examples 1 and 2 have larger differences in the contact angle, and have more favorable sensitivity with respect to the light irradiation, compared to Comparative Examples 1 to 3.

<<Measurement of XPS>>

An X-ray photoelectron spectrum (XPS) before and after exposure (exposure amount: 18 J/cm$^2$) of the substrate in which the silicon wafer pretreated using UV-ozone cleaner has been modified with the fluorine-containing compound (1) was measured. Table 4 shows relative intensity values obtained by setting the peak area value of a Si—Si bond in the silicon wafer to 1 and dividing the area of each element by each sensitivity.

TABLE 4

| | | Relative intensity | | |
|---|---|---|---|---|
| Measurement element | Chemical shift (eV) | Before exposure | After exposure | After exposure/ before exposure |
| Si—Si | 100 | 1 | 1 | 1 |
| Cl$_S$ (derived from CF$_3$, CF$_2$) | 292, 295 | 0.11 | 0 | 0 |
| N1s | 407 | 0.0066 | 0 | 0 |
| F1s | 681, 690 | 0.61 | 0.056 | 0.091 |

As shown in Table 4, it was found that the peak of the element based on a photodegradable group disappeared or significantly decreased compared to the peak area before exposure, and the photodegradable group was detached by exposure.

What is claimed is:

1. A fluorine-containing compound represented by a following general formula (1):

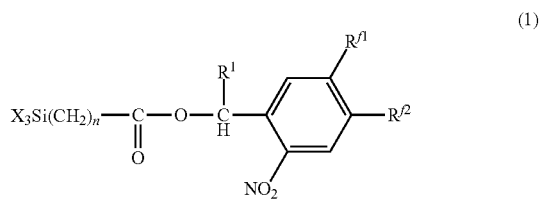

where X represents a halogen atom or a methoxy group, R$^1$ represents a branched chain or cyclic alkyl group having 3 to 10 carbon atoms, R$^{f1}$ and R$^{f2}$ represent fluorinated alkoxy groups having 5 to 10 carbon atoms, and n represents an integer of 0 to 20.

2. The fluorine-containing compound according to claim 1, wherein R$^1$ represents an isopropyl group, an isobutyl group, or a tert-butyl group.

3. The fluorine-containing compound according to claim 1, wherein R$^{f1}$ or R$^{f2}$ represent fluorinated alkoxy groups having 6 to 10 carbon atoms.

4. A substrate for pattern formation having a surface chemically modified with the fluorine-containing compound according to claim 1.

5. A photodegradable coupling agent formed of the fluorine-containing compound according to claim 1.

6. A pattern formation method for forming a pattern on a work surface of an object, the pattern formation method comprising:
chemically modifying the work surface using the fluorine-containing compound according to claim 1, by applying the fluorine-containing compound to the work surface such that the fluorine-containing compound bonds to the work surface;
generating a latent image formed of a hydrophilic region and a water repellent region by irradiating the chemically modified work surface with light having a predetermined pattern; and
disposing a pattern formation material in the hydrophilic region or the water repellent region.

7. A pattern formation method for forming a circuit pattern for an electronic device on a substrate having flexibility, the pattern formation method comprising:
chemically modifying an entire surface or a specific region of the substrate using the fluorine-containing compound according to claim 1, by applying the fluorine-containing compound to the entire surface or specific region of the substrate such that the fluorine-containing compound bonds to the entire surface or specific region of the substrate;
generating a latent image of the circuit pattern due to a difference in hydrophilicity and water repellency on the chemically modified surface of the substrate by irradiating with light energy having a distribution corresponding to the circuit pattern; and bringing a pattern formation material having fluidity into contact with a part of the latent image on the surface of the substrate and capturing the pattern formation material on the substrate in a shape of the circuit pattern by the difference in hydrophilicity and water repellency.

8. The pattern formation method according to claim 6, wherein the pattern formation material includes a liquid conductive material, a liquid semiconductor material, or a liquid insulating material.

9. The pattern formation method according to claim 6, wherein the light includes light having a wavelength included in a range of 200 nm to 450 nm.

10. The pattern formation method according to claim 6, wherein the applying the fluorine-containing compound to the work surface is performed by dipping or refluxing the substrate to treat the work surface.

11. The pattern formation method according to claim 7, wherein the applying the fluorine-containing compound to the entire surface or specific region of the substrate is performed by dipping or refluxing the substrate to treat the entire surface or specific region of the substrate.

* * * * *